United States Patent [19]

Schoenwald et al.

[11] Patent Number: 5,387,614

[45] Date of Patent: Feb. 7, 1995

[54] USE OF SIGMA RECEPTOR LIGANDS AS SALIVARY GLAND STIMULANTS

[75] Inventors: Ronald D. Schoenwald; Charles F. Barfknecht, both of Iowa City, Iowa

[73] Assignee: University of Iowa Research Foundation, Oakdale, Iowa

[21] Appl. No.: 97,534

[22] Filed: Jul. 27, 1993

[51] Int. Cl.6 ................... A61K 31/135; A61K 31/13
[52] U.S. Cl. ..................................... 514/654; 514/655
[58] Field of Search ................ 514/654, 655; 564/374, 564/391

[56] References Cited

U.S. PATENT DOCUMENTS 4,820,737  4/1989  Schoenwald ..................... 514/655

FOREIGN PATENT DOCUMENTS 1041013  9/1966  United Kingdom ................ 564/374

*Primary Examiner*—Alan Siegel
*Attorney, Agent, or Firm*—Zarley, McKee, Thomte, Voorhees, & Sease

[57] ABSTRACT

A method of stimulation salivary secretion comprising oral administration of certain sigma ligands which may be generally described as N,N-disubstituted phenylalkylamines.

4 Claims, 2 Drawing Sheets

USE OF SIGMA RECEPTOR LIGANDS AS SALIVARY GLAND STIMULANTS

BACKGROUND OF THE INVENTION

Diminished salivary gland output often results in the complaint of xerostomia (dry mouth). Salivary gland hypofunction is caused by a number of disorders or their treatments, including Sjögren's syndrome and radiation therapy for cancers of the head and neck. Dry mouth can cause impaired mastication, difficulty swallowing and ulcerations of the oral mucosa, and may even interfere with speech patterns and sleep.

Due to the diminished saliva, Sjögren's syndrome (SS) patients often experience a proliferation of bacteria resulting in tooth decay. The tongue often loses its protective papilla as well. SS patients are also more prone to oral yeast infections. Chapped lips and cracks at the corner of the mouth are also frequently experienced. Moreover, because of these symptoms, SS patients will often change their eating habits to avoid bulky foods (meats, breads, etc.). As a result, nutritional deficiencies may occur causing further complications.

To date, no satisfactory saliva substitute has yet been developed that has been able to duplicate the desirable properties of naturally occurring saliva. At best, saliva substitutes offer temporary relief. Nothing has so far been developed to reverse or halt the progression of diminished salivary gland production.

The approaches to search for treatments to manage salivary gland dysfunction have focused on four basic approaches. Those are (1) prevention; (2) management of the related clinical problems; (3) saliva substitutes; and (4) stimulation of secretions. These approaches to saliva substitutes have not met with any degree of success. Prevention and management of the related clinical problems only work in early stages. Saliva substitute and secretion stimulation deal with more chronic cases. There remain significant opportunities for development of successful treatments to stimulate secretions.

Stimulation of secretion has focused on three basic approaches, namely topical; systemic secretagogues (agents that will stimulate secretions); and finally, treatment of the underlying inflammatory condition.

The present invention represents a new approach to systemic secretagogues. None are currently available in the United States. Only one has generally been recognized on a world-wide basis as somewhat useful, and that is pilocarpine hydrochloride. Pilocarpine however is known to produce side effects involving the heart, blood pressure, and digestion. Moreover, it does not seem to stimulate the salivary gland to produce more saliva, but simply to release that which the patient has left. In other words, it only stimulates remaining functioning tissues, not increase salivary production as a whole. It can therefore be seen that there is a continuing and real need for the development of a safe and effective means for stimulating salivary function.

It has now been discovered that certain sigma site binding ligands can be administered successfully as a systemic secretagogue which is more effective than pilocarpine and yet does not cause side effects like pilocarpine.

The term "ligand" is used herein to generally describe the tissue binding portion of the active molecules referred to below. Some of these represent molecules which have earlier been found to be lacrimal stimulants, U.S. Pat. No. 4,820,737 and some have been found to be psychoactive sigma cite binding drugs, Schoenwald et al., Ser. No. 557,581, filed Jul. 24, 1990.

Pharmacological, biochemical and behavioral characterization of sigma binding sites is currently the focus of intense, widespread investigation. While the precise nature of sigma binding sites in cells is not quite known, many studies have suggested that it represents the site of action for a number of important drugs. For example, haloperidol, a butyrophenone antipsychotic, exhibits high affinity for sigma binding sites and several psychotominetics, including PCP and benzomorphan-type compounds (pentazocine), also bind at this site. Thus, strong binding sigma agents are indicative of usefulness in the treatment of schizophrenia.

In fact, several sigma compounds have been developed as antipsychotics. It is also believed that strong sigma site binding may also indicate therapeutic targets for epilepsy and brain ischemia.

In sum, the discovery of sigma binding sites has prompted investigation into the functional role of the sites. While the functional role is not precisely understood, it is nevertheless true that binding studies have revealed sigma sites which may exhibit a unique pharmacological profile, and have provided evidence favoring the existence of a multiplicity of sigma binding sites in the central nervous system.

The present invention is predicated upon the discovery that certain sigma ligands can be effective systemic secretagogues, and therefore, used to effectively treat dry mouth.

The primary objective of the present invention is to provide an effective salivary stimulant, which can be topically administered to selectively stimulate secretions in the oral cavity.

Another objective of the present invention is to provide compounds which are as effective, and in most cases, more effective than pilocarpine hydrochloride as systemic secretagogues, but which do not have the adverse side effects of pilocarpine hydrochloride.

Another objective of the present invention is to provide salivary stimulants that do not produce undesirable pharmacological side effects such as copious sweating, excessive salivation, gastric secretion and papillary constriction.

Another object of the present invention is to provide an orally effective salivary stimulant with action limited to the oral cavity, which has a reasonable duration of effect, and produces minimum side effects.

Another object of the present invention is to provide to the art the fundamental knowledge that salivary glands contain sigma receptors, and thus, some sigma site binding ligands are active in salivary stimulation.

The method and manner of accomplishing each of the above objectives as well as others will become apparent from the detailed description of the invention which follows hereinafter.

SUMMARY OF THE INVENTION

This invention relates to a method and composition for stimulating salivary secretion. The method comprises topically applying to the oral cavity a salivary secretion stimulating effective amount of certain sigma site binders, namely, N,N disubstituted alkyl phenylamines. Because the treatment involves stimulation of saliva production by the patient's own glands, as opposed to salivary substitutes, it is more effective than saliva substitutes, and importantly, it does not cause the side effects normally associated with systemic secretagogues such as pilocarpine hydrochloride.

DETAILED DESCRIPTION OF THE INVENTION

Figure 1:
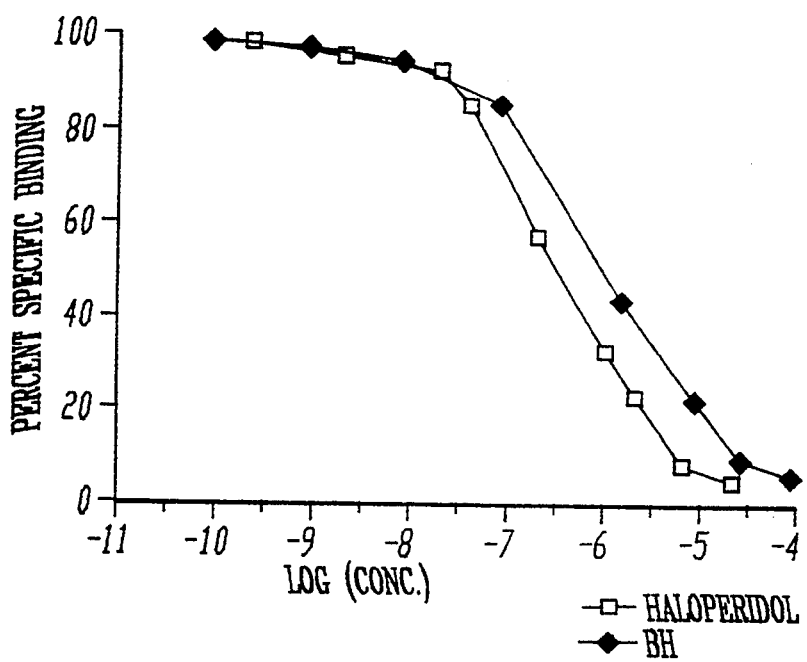
FIG. 1 shows comparison testing for a percent of specific binding of certain known sigma site binders used for comparison purposes.

In its broadest sense, this invention provides a method of topically applying to the oral cavity for treatment of dry mouth from whatever cause, including from those patients suffering from Sjögren's syndrome, of a small but salivary secretion inducing effective amount of certain sigma sigma binders. These compounds are arylalkylamines. In particular they are compounds that have the general formula:

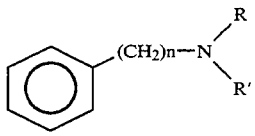

wherein:

n is a whole number and is from 1 to 8, and

R and R' may be the same or different and are selected from the group consisting of from $C_1$ to $C_8$ alkyl, phenyl and $C_3$ to $C_7$ cycloalkyl. The most preferred compound is N,N-dimethyl-2-phenylethylamine, wherein n=2 and R and R' are methyl.

Another preferred compound is that compound wherein n=3, R is methyl, and R' is cyclohexyl. Still another preferred compound is where n=2, R is methyl, and R' is cyclohexyl.

Certain other compounds, namely, N,N-disubstituted-2-phenylcyclopropylamines may also be used. The saliva stimulating compositions containing the above described active compounds will generally contain a salivary stimulating effective amount of the active in a pharmaceutically acceptable carrier, which may be administered through the mouth for transfer through mucous membrane to the salivary glands.

On a weight volume basis, it has been found that the amount of active may be within the range of 0.1% to about 5% and preferably from about 0.2% to about 0.6% be weight/volume basis. Amounts of the active compounds within these ranges dissolve in a suitable carrier have been demonstrated to be effective.

Suitable carriers for oral delivery are generally known and of course must be non-irritating, non-toxic, safe to swallow, and be pharmaceutically elegant for oral topical administration. Generally, for this invention, aqueous based systems wherein the carrier includes a buffer system to provide an oral cavity of safe pH, a chemical preservative, etc. Acceptable buffers should provide a composition having a pH within the range of from about 5.5 to about 7.8, preferable from about 6.8 to about 7.4. Chemically, generally those include phosphate, citrate, acetate, maleate, or mixtures thereof.

EXAMPLE

The following examples are offered to further illustrate but not limit the invention. As can be seen, the synthesis for these compounds is well known, involves routine chemistry, and need not be described in detail herein. However, generally, they may be synthesized in accordance with the procedures taught in the earlier referenced applications and patents of the present inventors.

In the following procedure it is demonstrated that salivary glands of New Zealand white rabbits contained sigma site receptors. In this procedure, New Zealand white rabbits were sacrificed using ½-1 ml of Beuthanasia-D Special (Schering Plough Animal Health, Keniworth, N.J.: 390 mg pentobarital sodium and 50 mg phenytoin sodium per ml) by injecting the preparation into the marginal ear vein. Whole submaxillary glands, free of blood, were dissected and either used immediately or frozen in cold 100 mM tris-HCl (pH 7.4) buffer. Glandular tissue was rinsed with cold 50 mM Tris-HCl (pH 7.4) followed by homogenization for 30 sec (Polytron, Brinkman Instr., setting 7). The homogenate was centrifuged at 800 rpm for 10 min at 4° C. to remove extraneous tissue. Then the supernatant was centrifuged at 75,000 Xg for 15 min at 4° C. (model L8-55, Preparative Ultracentrifuge, Beckman Instruments, Fullerton, Calif.). Following centrifugation, the pellet was homogenized again in 100 mM tris-HCl buffer and centrifuged at 75,000 Xg for 15 min. The resulting pellet containing the membrane fragments was suspended in Tris-HCl buffer to yield a concentration of 250 mg (wet wt) per mL. The method of Lowry et al. [Protein Measurement with the Folin Phenol Reagent. J. Biol. Chem., 193:265-275, 1951] was used to analyze for protein concentration which ranged from 20-40 mg/mL.

$^3$H-DTG (SA,39,4 CI/mmol, NEN) was incubated in 50 mM Tris-HCl (pH 7.4) at 4° C. for 60 min in membrane homogenate suspensions (concentrations ranged from 1/5th to 5-fold greater than the calculated $K_d$). Spiperone (25 nM) was added to prevent binding to $D_2$ dopamine or $5HT_2$ serotonin receptors. Incubation was stopped with the addition of 4 mL cold 100 mM Tris-HCl (pH 7.4) followed by vacuum filtration through glass microfiber filters (Whatman GF/C filters) that had been pretreated with 0.5% polyethyleneimine for 15 min. After filtration, the precipitate (radioligand bound to s-receptor) was washed twice with 50 mM Tris-HCl buffer (pH 7.4) at room temperature. The filter, containing the precipitate, was transferred to a scintillation vial containing 1 mL of tissue solubilizer (Soluene 350, Packard Inst.) and 4 mL of scintillation fluid (Budget Solve, Fisher Scientific, Fair Lawn, N.J.) and counted (Beckman LS 3801). Nonspecific binding (NSB) was determined by saturating the system with nonradioactive haloperidol (10 M) for $^3$H-DTG binding. Specific binding was determined by subtracting NSB from total binding, The affinity or dissociation constant, $K_d$, and the number of binding sites, $B_{max}$ were calculated according to methods outlined by Yamamura et al. (Unnerstall, J. R. Computer-assisted Analysis of Binding Data. In Methods in Neurotransmitter Receptor Analysis. Yamamura, H. I., Enna, J. S. and Kuhar, M. J., eds, Raven Press, New York, 1990, p.

37-68.) and from the use of nonlinear computer curve-fitting programs (McPherson, G. A., A Practical Computer-Based Approach to the Analysis of Radioligand Binding Experiments. Comput. Programs Biomed., 17: 107-114, 1983; and Munson, P. J. and Rodbard, D. LIGAND: A Versatile Computerized Approach for Characterization of Ligand-Binding Systems. Anal. Biochem., 107: 220-239, 1980).

The observations of effective salivary stimulation actually occurred during use of the most preferred compound wherein N=2, and R and R" are methyl, as dry eye syndrome treatment. It was noticed that whenever the rabbit eye was dosed topically, copious amounts of saliva flowed from about one half of the rabbits. This led to further investigations of this and other compounds as a means of treating dry mouth associated with, for example, Sjögren's syndrome. The present compound for example could be formulated into a conventional lozenge for a topical application directly in the oral cavity to stimulate saliva flow. Such lozenges can either be made by dissolving the drug in water, adding powdered sugar, flavor and a gum (e.g., 7% powdered acacia) to give sufficient adhesiveness. This type of lozenge is harder than a conventional tablet, but dissolves slowly. The lozenge formulation is made by compressing the formula on a tablet press according to the art.

Competition studies demonstrate the selective sigma binding to compounds of the present invention in comparison to Haloperidol a known sigma site binder.

Radioligand Competition Experiments $^3$H-DTG (5 nM, New England Nuclear Research Products, Boston, Mass.) or 3H-haloperidol (16.75 nM, New England Research Products) was incubated with sigma receptors and increasing concentrations of each BHY derivative ($10^{-9}$ to $10^{-2}$M) in 50 mN Tris-HCl (pH 7.4) at 4° C. for 60 minutes in membrane homogenate suspensions. Spiperone (25 nM) was added to prevent binding to $D_2$ dopamine, or $5HT_2$ serotonin receptors. A volume of 5 mL cold 100 mM Tris-HCl (pH 7.4) was added to the incubation. The mixture was vacuum filtered through glass microfiber filters (Whatman GF/C filters) which had been pretreated with 0.5% polyethyleneimine for 15 min. After filtration, the precipitate (radioligand bound to the sigma receptor) was washed twice with 100 mM Tris-HCl buffer (pH 7.4) at room temperature. The filter along with the adhering precipitate was transferred to a scintillation vial containing 1 mL of tissue solubilizer (Soluene 350, Packard Inst., Downers Grove, Ill.) and 4 mL of scintillation fluid (Budget Solve, Fisher Scientific, Fair Lawn, N.J.) and counted (Beckman LS 3801). Nonspecific binding (NSB) was determined separately by saturating the system with nonradioactive haloperidol ($10^{-3}$M) in the presence of $^3$H-DTG binding. Specific binding was determined by subtracting NSB from total binding. $IC_{50}$ values, the concentration that binds to 50% of the available sites, were calculated using graphical methods.

Radioligand Binding

Using membrane homogenate suspensions of acini cells (100,000 Hg fraction) obtained from the submaxillary gland of white New Zealand rabbits, an analyses of the binding data (Scatchard plot) revealed a single binding site for $^3$H-DTG with a $K_d$ of 6.0±1.2 nM and a $B_{max}$ of 68.4±7.2 nM/mg of protein. These results identify and characterize the sigma-binding site.

Radioligand Competition Experiments

Figure 2:
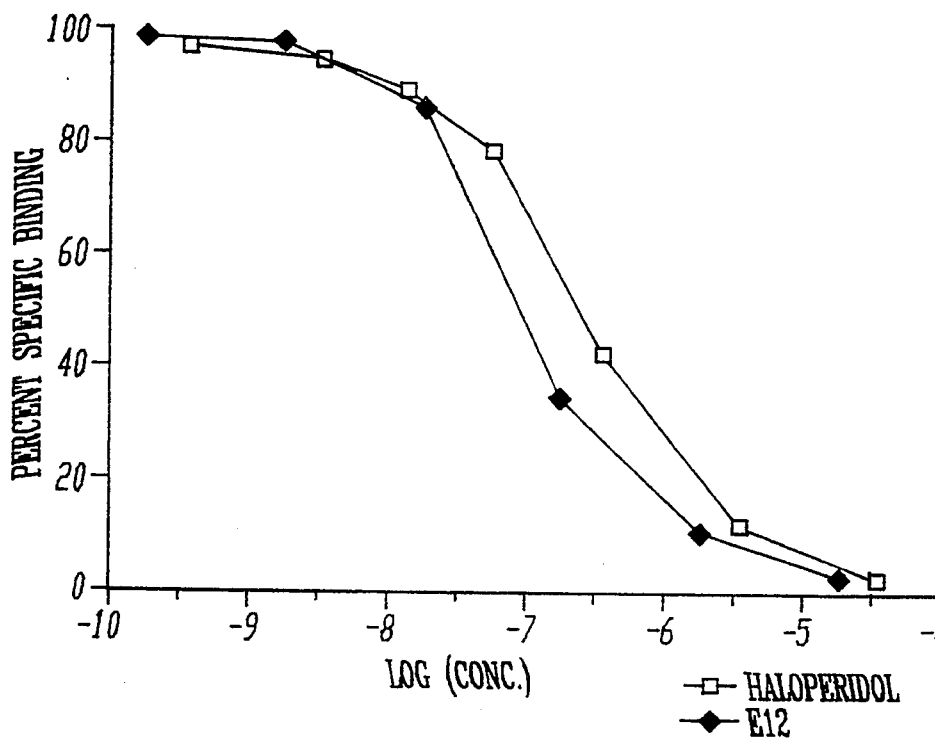
FIG. 2 shows comparison testing between Haloperidol and compound wherein n=3, R is methyl, and R' is cyclohexyl.
Figure 3:
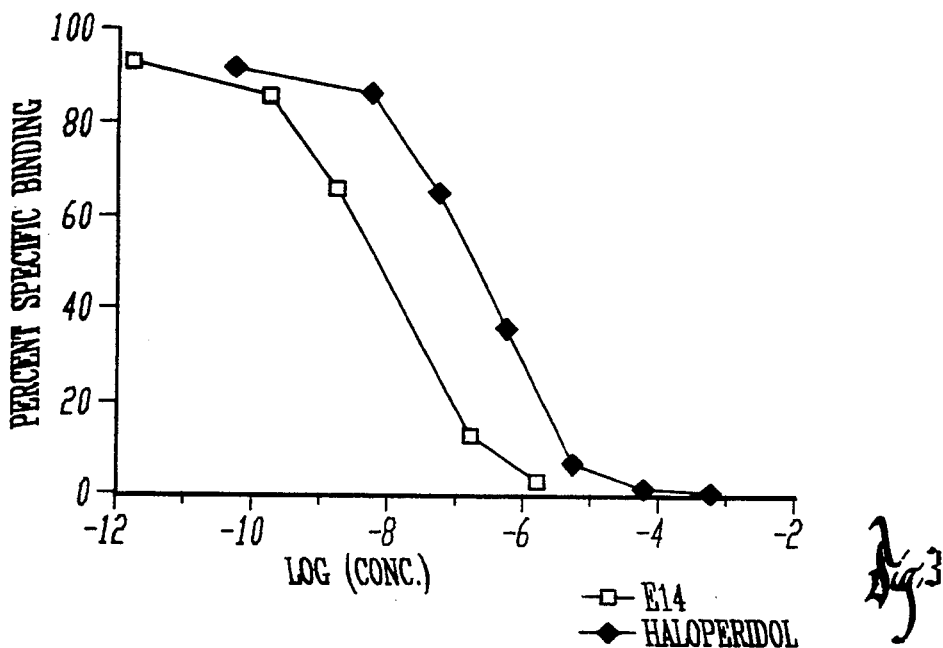
FIG. 3 shows competition testing for sigma site specific binding for the compound wherein n is 2, R is methyl, and R' is cyclohexyl.
Figure 4:
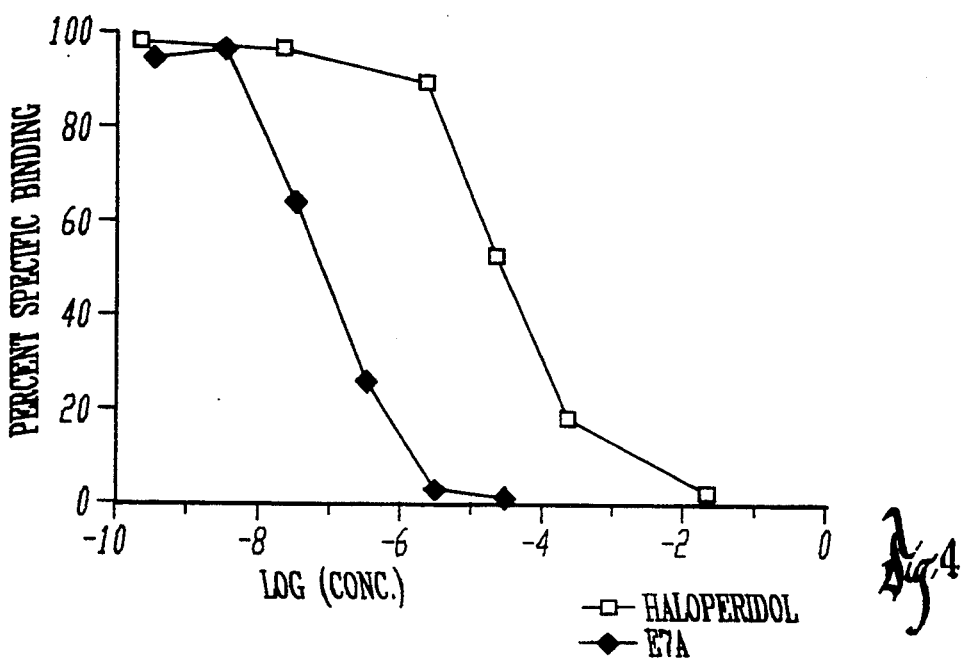
FIG. 4 shows competition testing for sigma site binding for the most preferred compound wherein n=2, and R and R' are methyl.

Typical results of competition experiments are shown in the graphs of the drawings, FIG. 1-4. The averaged $IC_{50}$ values for haloperidol (reference compound), bromhexine, E12, E14 and E7A are 241±59.7 nM (n=7), 690±276 nM (n=2), 64.1±35.3 nM (n=3) 10.5±5 nM (n=2) and 294.4±233M (n=5) nM. The sigma receptors in the maxillary gland are yielding $IC_{50}$ values that indicate a lower affinity for the radioligand ($^3$H-DTG) than other exocrine glands.

From the above results, it can be seen that the compounds of the present invention are effective sigma ligands as salivary stimulants.

It is intended that the invention as defined in the appended claims cover what is specified in the claims and those matters rightfully within the scope of the present invention by proper application of the doctrine of equivalence to claims.

What is claimed is:

1. A method of stimulating salivary secretion, comprising;

orally administering a small but saliva stimulating effective amount of a compound of the formula:

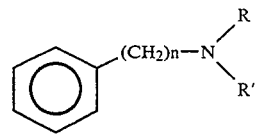

wherein n is from 1 to 8 and R and R' may be the same of different and are selected from the group consisting of $C_1$ to $C_8$ alkyl, $C_3$ to $C_7$ cycloalkyl.

2. The method of claim 1 wherein n=2 and R and R' are methyl.

3. The method of claim 1 wherein n=3, R is methyl and R' is cyclohexyl.

4. The method of claim 1 wherein n=2, R is methyl and R' is hexyl.

* * * * *